United States Patent [19]
Radcliffe et al.

[11] Patent Number: 5,406,011
[45] Date of Patent: Apr. 11, 1995

[54] PROCESS FOR THE DEHYDROGENATION OF PARAFFINIC HYDROCARBONS

[75] Inventors: William H. Radcliffe, Des Plaines; Thomas R. Fritsch, Wheaton; Bipin V. Vora, Darien, all of Ill.

[73] Assignee: UOP, Des Plaines, Ill.

[21] Appl. No.: 223,786

[22] Filed: Apr. 6, 1994

[51] Int. Cl.⁶ .............. C07C 5/00; C07C 1/00; C07C 5/327; C07C 5/333
[52] U.S. Cl. .............. 585/254; 585/264; 585/315; 585/324; 585/655; 585/659
[58] Field of Search .............. 585/254, 264, 315, 324, 585/655, 659

[56] References Cited

U.S. PATENT DOCUMENTS 4,761,509  8/1988  Vora et al. ............ 585/254
5,012,021  4/1991  Vora et al. ............ 585/315

Primary Examiner—Anthony McFarland
Assistant Examiner—Nhat D. Phan
Attorney, Agent, or Firm—Thomas K. McBride; John G. Tolomei; John G. Cutts, Jr.

[57] ABSTRACT

An improved process for the catalytic dehydrogenation of paraffinic hydrocarbons is disclosed. Feed paraffinic hydrocarbons are dehydrogenated by means of contacting the dehydrogenatable hydrocarbon with a dehydrogenation catalyst in a first dehydrogenation zone wherein the endothermic dehydrogenation reaction reduces the temperature of the resulting hydrocarbon stream containing dehydrogenated hydrocarbon compounds. The resulting effluent from the first dehydrogenation zone is then contacted with a stream of gas comprising normally gaseous hydrocarbon compounds having a temperature greater than the hydrocarbon stream to increase the temperature of the hydrocarbon stream and then introducing the resulting heated stream into a second dehydrogenation zone to produce additional dehydrogenated hydrocarbon compounds.

7 Claims, 1 Drawing Sheet

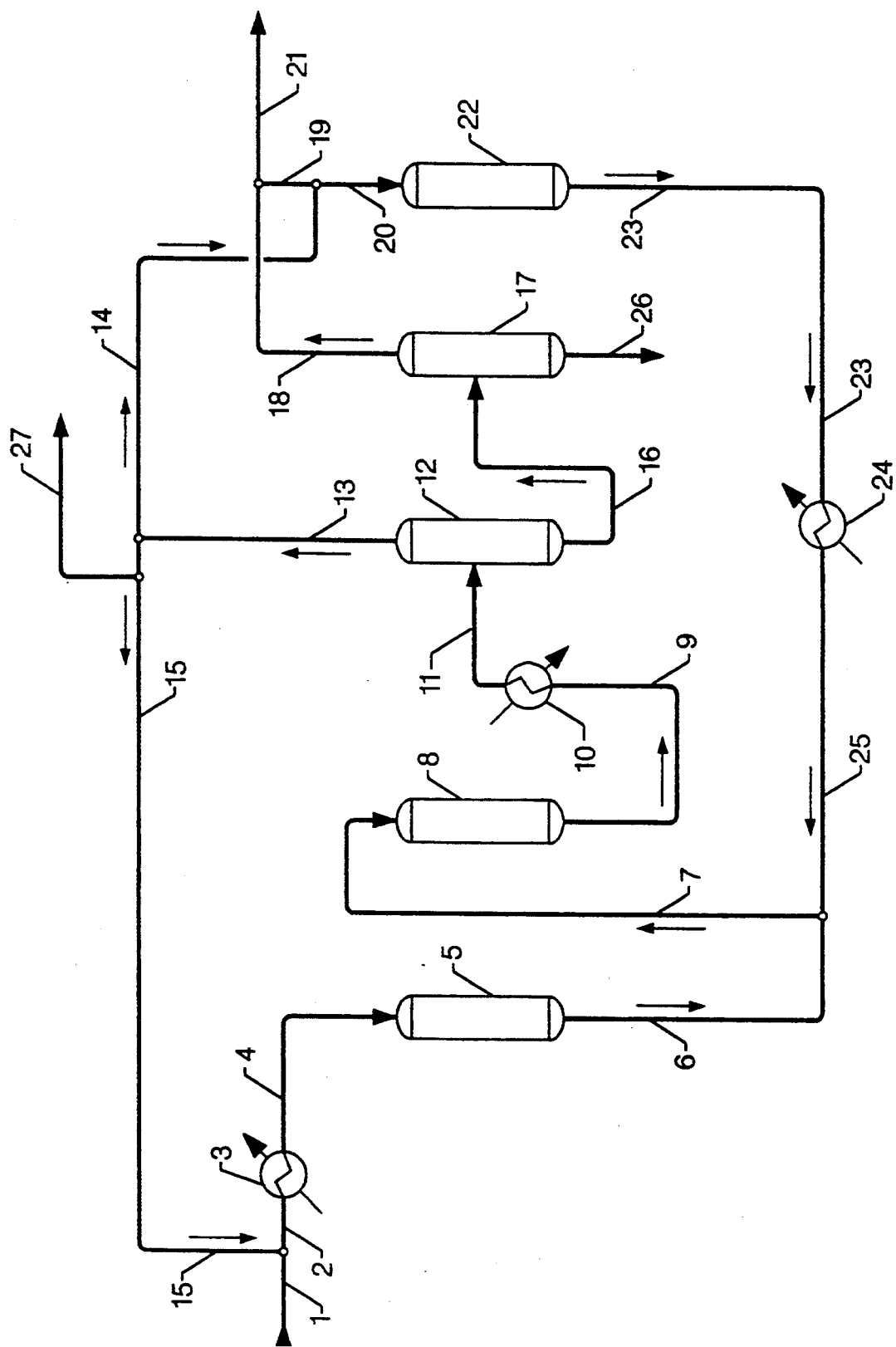

PROCESS FOR THE DEHYDROGENATION OF PARAFFINIC HYDROCARBONS

BACKGROUND OF THE INVENTION

The field of art to which this invention pertains is the production of olefinic hydrocarbons. More specifically, the invention relates to a hydrocarbon conversion process for the selective catalytic dehydrogenation of acyclic paraffinic hydrocarbons to produce monoolefinic hydrocarbons.

INFORMATION DISCLOSURE

U.S. Pat. No. 4,761,509 discloses a process for the catalytic dehydrogenation of paraffinic hydrocarbons.

The prior art utilizes large commercial reactors which are essentially adiabatic. In the case of endothermic reactions, the reaction temperature decreases as the reaction proceeds which lowers the equilibrium conversion level and, accordingly, the achievable conversion level is decreased. In order to overcome this problem, the prior art used tubular reactors so that heat can be supplied externally via heat-exchange through the tubes into the reaction zone. Tubular reactors are disadvantageous for large scale reactor systems because catalyst loading and unloading becomes an onerous and expensive operation.

Endothermic hydrocarbon conversion reactions such as dehydrogenation and dehydrocyclization are conducted while employing hydrogen co-feed in order to suppress undesirable side reactions and catalyst deactivation due to coke formation on the catalyst.

Previously, it has been known to provide the heat of reaction in multi-stage catalytic reactions by reheating the entire effluent from one catalyst zone before it enters the next catalyst zone. This results in additional pressure drop in the system which requires a higher inlet pressure and which is disadvantageous and detrimental to the dehydrogenation equilibrium. In a typical prior art heater-reactor design, as high as 80% of the total pressure drop occurs in the heater and the inlet lines to the reactor. Furthermore, putting the entire first stage reactor effluent through a heater adds thermal residence time as well as exposes the product to high skin (wall) temperature. Dehydrogenation zone effluents are prone to thermal cracking and also have a tendency of forming coke on heat-exchange surfaces. Modem catalytic dehydrogenation processes have served the industry well, but have been handicapped by the multiple reaction zones which are necessarily required for commercial service.

Based upon a recognition of the shortcomings of the prior art, we have discovered an improved process for the dehydrogenation of hydrocarbon compounds wherein the required heat for a second dehydrogenation zone is provided by introducing a heated stream of gas comprising normally gaseous hydrocarbons recovered from a product stripper. Therefore, it is desired that high temperature, non-catalytic residence time be minimized in accordance with the present invent/on.

BRIEF SUMMARY OF THE INVENTION

It has now been found that an improved dehydrogenation process can be achieved by reheating the effluent from one dehydrogenation zone with a hot stream of gas comprising normally gaseous hydrocarbons from a product stripper before introducing the feed stream to a second catalytic dehydrogenation zone. In accordance with the present invention, if the improved process is operated in order to achieve a constant conversion, a higher yield of olefinic hydrocarbons is achieved while utilizing lower reactor temperatures which results in improved catalyst life and process plant operability. When the present invention is utilized and is operated at increased conversion, the same yield is expected while enjoying an increased capacity of a significant amount which results in reduced operating costs.

The invention provides a process for the dehydrogenation of a paraffinic dehydrogenatable hydrocarbon by means of contacting the dehydrogenatable hydrocarbon with a dehydrogenation catalyst in a first alehydrogenation zone wherein the endothermic dehydrogenation reaction reduces the temperature of the resulting hydrocarbon stream containing dehydrogenated hydrocarbon compounds. The resulting effluent from the first dehydrogenation zone is then contacted with a hot stream of gas comprising normally gaseous hydrocarbons from a product stripper having a temperature greater than the hydrocarbon stream to increase the temperature of the hydrocarbon stream and then introducing the resulting heated stream into a second dehydrogenation zone to produce additional dehydrogenated hydrocarbon compounds. The use of a heater for the gas comprising normally gaseous hydrocarbons in accordance with the present invention adds very little pressure drop to the system and the hot stream of gas comprising normally gaseous hydrocarbons may be conveniently introduced and admixed with the flowing hydrocarbon stream close to the catalyst bed to minimize thermal degradation.

One broad embodiment of the present invention is a process for the dehydrogenation of a paraffinic dehydrogenatable hydrocarbon which process comprises: (a) contacting the paraffinic dehydrogenatable hydrocarbon with a dehydrogenation catalyst at alehydrogenation conditions in a first dehydrogenation zone wherein the endothermic dehydrogenation reaction reduces the temperature of a resulting hydrocarbon stream containing dehydrogenated hydrocarbon compounds; (b) contacting the hydrocarbon stream containing dehydrogenated hydrocarbon compounds produced in step (a) with a first stream of gas comprising normally gaseous hydrocarbon compounds having a temperature greater than the hydrocarbon stream to thereby increase the temperature of the hydrocarbon stream to dehydrogenation conditions; (c) contacting a resulting heated hydrocarbon stream produced in step (b) with a dehydrogenation catalyst at dehydrogenation conditions in a second dehydrogenation zone; (d) condensing at least a portion of an effluent from the second alehydrogenation zone to produce a liquid hydrocarbon stream comprising dehydrogenated hydrocarbon compounds and dissolved normally gaseous hydrocarbon compounds and a hydrogen-rich gaseous stream; (e) separating the liquid hydrocarbon stream comprising dehydrogenated hydrocarbon compounds and dissolved normally gaseous hydrocarbon compounds to produce a second stream of gas comprising normally gaseous hydrocarbon compounds; (f) introducing at least a portion of the second stream of gas comprising normally gaseous hydrocarbon compounds from step (e) and at least a portion of the hydrogen-rich gaseous stream from step (d) into an olefin hydrogenation zone; (g) heating at least a portion of the effluent from the olefin hydrogenation zone to produce the first stream of gas comprising normally gaseous hydrocarbon compounds of step (b); and (h) recovering dehydrogenated hydrocarbon compounds.

Other embodiments of the present invention encompass further details such as sources of hydrocarbon feed streams, alehydrogenation catalysts and dehydrogenation operating conditions, all of which are hereinafter disclosed in the following discussion of each of these facets of the invention.

BRIEF DESCRIPTION OF THE DRAWING

The drawing is a simplified process flow diagram of a preferred embodiment of the present invention.

DETAILED DESCRIPTION OF THE INVENTION

The production of acyclic olefinic hydrocarbons is a highly useful hydrocarbon conversion process. The product olefinic hydrocarbons find utility in the production of a wide variety of useful chemicals including synthetic lubricants, detergents, polymers, alcohols, plasticizers, etc.

The feed hydrocarbon charged to the subject process is an acyclic $C_7^+$ hydrocarbon. Preferably, the feed hydrocarbon is a normal paraffin. The upper limit on the carbon number of the charge stock is basically set by the volatility and processability of the charge stock in the dehydrogenation reactor. This upper limit is at about $C_{22}$ paraffins. The feed stream may be a high purity stream of a single paraffin or a feed stream may comprise a mixture of two or more paraffins having different carbon numbers. For instance, an admixture of $C_{10}$ to $C_{15}$ normal paraffins is often passed through a dehydrogenation zone to produce linear olefins which are consumed in the production of linear alkyl benzenes suitable for use in the production of biodegradable detergents. In accordance with the present invention, the paraffinic dehydrogenatable hydrocarbon preferably comprises $C_{10}$ to $C_{20}$ paraffins.

The equipment used in the process of the present invention is preferably configured substantially as shown in the drawing which is hereinafter described in detail, however, additional dehydrogenation zones are also contemplated. In accordance with the present invention, two or more dehydrogenation zones may be utilized. In this arrangement, a fresh paraffinic hydrocarbon feed stream is combined with a hydrogen-rich recycle gas stream. This forms a reactant stream which is heated by indirect heat exchange and is then passed through a bed of a suitable catalyst maintained at the proper alehydrogenation conditions of temperature and pressure. The effluent of this catalyst bed or reactor effluent stream is then contacted with a hot stream of gas comprising normally gaseous hydrocarbons from a product stripper which is utilized to raise the temperature of the reactant stream before introduction into a second catalyst bed. The effluent from the second catalyst bed or reactor effluent stream is cooled and partially condensed. Part of the uncondensed material is employed as the hydrogen-rich recycle gas stream. The remainder of the uncondensed hydrogen-rich material is the net production of hydrogen which may be used in other applications such as desulfurization, for example. As used herein, the term "rich" is intended to indicate a molar concentration of the indicated compound or class of compounds above 50%. The separation zone also produces a liquid stream referred to herein as the liquid phase process stream. This stream is basically an admixture of dehydrogenated and undehydrogenated acyclic hydrocarbons. This liquid phase stream also contains some dissolved hydrogen and light hydrocarbons produced in various cracking reactions which occur at the high temperatures employed in the alehydrogenation reactor. In accordance with the present invention, this resulting liquid effluent stream is passed into a product stripping column designed and operated to remove overhead all compounds which are more volatile than the lightest hydrocarbon which it is desired to have present in the net effluent stream of the dehydrogenation process. These lighter materials will be concentrated into a net overhead gaseous stream which will comprise an admixture of hydrogen and light normally gaseous hydrocarbons. The purpose of the stripping operation is to prevent the entrance of volatile light materials including hydrogen into downstream processing zones where they would present certain operational problems and to prepare a gaseous stream which is subsequently heated and used to increase the temperature of hydrocarbon reactants before being introduced into a subsequent dehydrogenation zone. For example, the passage of light monoolefins into an alkylation zone would lead to the production of an increased amount of undesired side products through alkylation and polymerization reactions. Other non-condensable materials under the alkylation conditions, such as hydrogen, methane and ethane, would require venting which will require scrubbing for hydrogen fluoride removal which creates waste disposal problems. The stripping column also serves to eliminate the light hydrocarbons from any recycle stream which returns paraffinic hydrocarbons to the dehydrogenation zone from a downstream processing unit. In a second case when the separation zone produces a liquid stream which contains diolefins, this liquid stream may be subjected to selective hydrogenation to convert diolefin compounds to monoolefin compounds before the liquid stream having a lower concentration of diolefins is passed into the stripping column.

The composition of the dehydrogenation catalyst is not believed to materially affect the operation of the subject process provided this catalyst meets commercial standards for activity, stability, and selectivity. Dehydrogenation catalysts are described in U.S. Pat. Nos. 3,274,287; 3,315,007; 3,315,008; 3,745,112; and 4,430,517. These catalysts comprise a platinum group component supported on a porous carrier material. The preferred carrier material is a refractory inorganic oxide such as gamma-alumina. The preferred alehydrogenation catalysts contain on an elemental basis 0.01 to 2 wt. % platinum group component and about 0.1 to 5 wt. % of an alkali or alkaline earth metal. Preferably, there is present 0.05 to 1 wt. % platinum group component and about 0.25 to 3.5 wt. % of the alkali or alkaline earth component. The platinum group component may be chosen from the group consisting of platinum, palladium, rhodium, ruthenium, osmium and iridium, but platinum is highly preferred. The alkali or alkaline earth component may be selected from the group consisting of the alkali metals-cesium, rubidium, potassium, sodium, and lithium; and the alkaline earth metals-calcium, strontium, barium, and magnesium. This component is preferably either lithium or potassium. Another example of a suitable dehydrogenation catalyst is a catalyst which, in addition to the previously described platinum and alkali or alkaline earth metal components, contains a tin component. This catalytic composite would contain from 0.1 to about 1 wt. % tin. Yet another catalytic composite which should be highly suited for use in the subject process comprises an indium component in addition to the platinum, tin and alkali or alkaline earth components. The indium component may be present on an elemental basis equal to about 0.1 to about 1 wt. % of the final composite. It is also known in the art that some catalytic composites of this nature may benefit from the presence of a small amount of a halogen component, with chlorine being the normally preferred halogen. Typical halogen concentrations in the final catalytic composite range from about 0.1 to about 1.5 wt. %. A halogen component is not desired in all situations. These catalytic composites are known to those skilled in the art and are described in the available references.

In accordance with the present invention, dehydrogenation conditions include a pressure from about 0 psig to about 50 psig (345 kPa gauge) and a temperature from about 752° F. (400° C.) to about 1022° F. (550° C.). The temperature of the stream of gas comprising normally gaseous hydrocarbons from a product stripper which is utilized to heat the hydrocarbon feed to reaction temperature is preferably from about 932° F. (500° C.) to about 1292° F. (700° C.).

The net product of the process, the bottoms stream of the stripping column, can be passed into a number of downstream processing units or it can be withdrawn as a finished product. For instance, the product stream may be passed into alkylation zones wherein the olefinic hydrocarbons can be reacted with aromatic hydrocarbons or into esterification zones as in the production of plasticizers. The product stream may also be passed into an oligomerization zone or a hydration zone. Another possibility is that the net process effluent stream may be charged to a separation zone which separates the mono-olefins from the unconverted paraffins. This separation could be performed by fractional distillation on a single carbon number effluent stream but would be quite a difficult and expensive fractionation. Sorptive-type separations which employ selective solid adsorbents, known in the art, are preferred for this type of separation. A broad carbon number range olefin-paraffin mixture can be charged to such a process and efficiently separated into a high purity olefin stream and a paraffin stream. The paraffin stream may then be recycled to the dehydrogenation zone.

In accordance with the present invention, the olefin hydrogenation zone is used to saturate relatively small quantities of olefinic hydrocarbon compounds which are present in the stream of normally gaseous hydrocarbon compounds and recovered from the product stripper. The presence of olefinic hydrocarbons is undesirable because they tend to polymerize and form coke deposits in the heater during the heating to the desired process temperature. The olefin hydrogenation zone is preferably maintained at conditions selected to hydrogenate olefins and under an imposed pressure from about 10 psig to about 200 psig, a maximum catalyst bed temperature in the range from about 100° F. (38° C.) to about 400° F. (204° C.) and hydrogen flow rates from about 100 standard cubic feet per barrel (SCFB) to about 1500 SCFB.

The preferred catalytic composite disposed within the hereinabove-described olefin hydrogenation zone can be characterized as containing a metallic component having hydrogenation activity, which component is combined with a suitable refractory carrier material of either synthetic or natural origin. The precise composition and method of manufacturing the carrier material is not considered essential to the present invention. Preferred carrier materials are alumina, silica, carbon and mixtures thereof. Suitable components having hydrogenation activity are those selected from the group comprising the metals of Group VIB and VIII of the Periodic Table, as set forth in the *Periodic Table of Elements,* E. H. Sargent and Company, 1964. Thus, the catalytic composite may comprise one or more metallic components from the group of molybdenum, tungsten, chromium, iron, cobalt, nickel, platinum, palladium, iridium, osmium, rhodium, ruthenium and mixtures thereof. The concentration of the catalytically active metallic component, or components, is primarily dependent upon a particular metal as well as the characteristics of the hydrocarbon feedstock to the olefin hydrogenation zone. For example, the metallic components of Group VIB are generally present in an amount within the range from about 1 to about 20 weight percent, the iron-group metals in an amount within the range of about 0.2 to about 10 weight percent, whereas the noble metals of Group VIII are preferably present in an amount within the range of from about 0.1 to about 5 weight percent, all of which are calculated as if these components existed within the catalytic composite in the elemental state.

In the drawing one embodiment of the present invention is illustrated by means of a simplified flow diagram in which such details as pumps, instrumentation, heat exchange and heat-recovery circuits, compressors and similar hardware have been deleted as being non-essential to the understanding of the techniques involved. The use of such miscellaneous equipment is well within the purview of one skilled in the art of petroleum refining and petrochemical production techniques.

Referring now to the drawing, a paraffin feed stream comprising an admixture of $C_{10}$–$C_{15}$ normal paraffins enters the process through line 1. This feed stream is admixed with a hydrogen-rich gaseous stream supplied via line 15 and is passed by line 2 into heater 3 to achieve reaction temperature. The resulting heated feed stream is removed from heater 3 and is introduced via line 4 into reaction zone 5 which is operated at alehydrogenation conditions. The effluent from reaction zone 5 is transported via line 6 and is admixed with a heated stream of gas comprising normally gaseous hydrocarbons provided via line 25 to form a heated reactant stream which is introduced via line 7 into reaction zone 8. The resulting effluent containing dehydrogenated hydrocarbons is removed from reaction zone 8 via line 9 and introduced into heat exchanger 10. Heat exchanger 10 is used to cool the flowing stream and line 11 is used to transport the resulting cooled stream into vapor-liquid separator 12. A resulting liquid stream containing dehydrogenated hydrocarbon compounds and dissolved normally gaseous hydrocarbons is removed from vapor-liquid separator 12 via line 16 and introduced into stripper 17. A resulting liquid stream containing dehydrogenated hydrocarbon compounds and having a reduced concentration of normally gaseous hydrocarbons is removed from stripper 17 via line 26 and recovered. A stream containing normally gaseous hydrocarbons is removed from stripper 17 via line 18 and at least a portion is introduced into olefin hydrogenation zone 22 via line 19 and line 20. A hydrogen-rich gaseous stream is removed from vapor-liquid separator 12 via line 13 and a net hydrogen gas stream is removed from the process via line 27. Another portion of the hydrogen-rich gaseous stream resulting from vapor-liquid separator 12 is transported via fine 13 and line 14 and is admixed with normally gaseous hydrocarbons supplied via line 19 and the resulting admixture is introduced into olefin hydrogenation zone 22 via line 20. A stream containing normally gaseous hydrocarbons having a reduced concentration of olefin hydrocarbons is removed from olefin hydrogenation zone 22 via line 23 and introduced into heat exchanger 24 wherein the temperature of the flowing stream is increased. The resulting heated normally gaseous hydrocarbon stream is removed from heat exchanger 24 and transported via line 25 as hereinabove described. Another portion of the hydrogen-rich gaseous stream which is removed from vapor-liquid separator 12, transported via line 13 and line 15, and is admixed with the incoming fresh hydrocarbon feed as hereinabove described.

The process of the present invention is further demonstrated by the following illustrative embodiment. This illustrative embodiment is, however, not presented to unduly limit the process of this invention, but to further illustrate the advantages of the hereinabove-described embodiments. The following data were not obtained by the actual performance of the present invention, but are considered prospective and reasonably illustrative of the expected performance of the invention.

ILLUSTRATIVE EMBODIMENT

A paraffin feed stream comprising an admixture of $C_{10}$–$C_{15}$ normal paraffins is introduced into a dehydrogenation zone containing a dehydrogenation catalyst comprising alumina and platinum and maintained at dehydrogenation conditions including a molar hydrogen to normal paraffin ratio of 6:1, a reactor inlet temperature of 882° F. (472° C.) and a pressure of 20 psig. The reactor effluent contained 12 mol percent monoolefin. This is identified as Run A.

Another paraffin feed stream having the same characteristics as the feed stream in Run A is converted in a dehydrogenation zone containing a dehydrogenation catalyst comprising alumina and platinum with one-half of the catalyst located in a first reactor and one-half of the catalyst located in a second reactor. The total volume of catalyst was the same as in Run A. The feed stream is introduced into the first reactor in admixture with about 80% of the total hydrogen used in Run A at a reactor inlet temperature of 472° C. and a pressure of 20 psig. The effluent from Reactor 1 is admixed with a gaseous stream comprising 75 mol percent normally gaseous hydrocarbon compounds and 25 tool percent hydrogen having a temperature of 1100° F. (593° C.) to produce a feed having a temperature of 882° F.(472° C.) which is introduced into Reactor 2. The effluent from Reactor 2 contained 15 tool percent monoolefin. This is identified as Run B. The results of Run A and Run B are summarized and presented in Table 1.

TABLE 1

| SUMMARY OF RESULTS | | |
|---|---|---|
| | A | B |
| Reactor 1, Catalyst Volume, % | 100 | 50 |
| Reactor 2, Catalyst Volume, % | — | 50 |
| Hydrogen to Reactor 1, % | 100 | 80 |
| Hydrogen to Reactor 2, % | — | 20 |
| Reactor 1, Inlet Temperature, °C. | 472 | 472 |
| Reactor 2, Inlet Temperature, °C. | — | 472 |
| Monoolefins, mol % | 12 | 15 |

The foregoing description, drawing and illustrative embodiment clearly illustrate the advantages encompassed by the process of the present invention and the benefits to be afforded with the use thereof.

What is claimed:

1. A process for the dehydrogenation of a paraffinic dehydrogenatable hydrocarbon which process comprises:
   (a) contacting said paraffinic dehydrogenatable hydrocarbon with a dehydrogenation catalyst at dehydrogenation conditions in a first dehydrogenation zone wherein the endothermic dehydrogenation reaction reduces the temperature of a resulting hydrocarbon stream containing dehydrogenated hydrocarbon compounds;
   (b) contacting said hydrocarbon stream containing dehydrogenated hydrocarbon compounds produced in step (a) with a first stream of gas comprising normally gaseous hydrocarbon compounds having a temperature greater than said hydrocarbon stream to thereby increase the temperature of said hydrocarbon stream to dehydrogenation conditions;
   (c) contacting a resulting heated hydrocarbon stream produced in step (b) with a dehydrogenation catalyst at dehydrogenation conditions in a second dehydrogenation zone;
   (d) condensing at least a portion of an effluent from said second dehydrogenation zone to produce a liquid hydrocarbon stream comprising dehydrogenated hydrocarbon compounds and dissolved normally gaseous hydrocarbon compounds and a hydrogen-rich gaseous stream;
   (e) separating said liquid hydrocarbon stream comprising dehydrogenated hydrocarbon compounds and dissolved normally gaseous hydrocarbon compounds to produce a second stream of gas comprising normally gaseous hydrocarbon compounds;
   (f) introducing at least a portion of said second stream of gas comprising normally gaseous hydrocarbon compounds from step (e) and at least a portion of said hydrogen-rich gaseous stream from step (d) into an olefin hydrogenation zone;
   (g) heating at least a portion of the effluent from said olefin hydrogenation zone to produce said first stream of gas comprising normally gaseous hydrocarbon compounds of step (b); and
   (h) recovering dehydrogenated hydrocarbon compounds from said liquid hydrocarbon stream comprising dehydrogenated hydrocarbon compounds and dissolved normally gaseous hydrocarbon compounds produced in step (d).

2. The process of claim 1 wherein said paraffinic dehydrogenatable hydrocarbon comprises $C_{10}$ to $C_{15}$ paraffins.

3. The process of claim 1 wherein said paraffinic dehydrogenatable hydrocarbon comprises $C_{15}$ to $C_{20}$ paraffins.

4. The process of claim 1 wherein said dehydrogenation conditions include a pressure from about 0 psig to about 50 psig (345 kPa gauge) and a temperature from about 752° F. (400° C.) to about 1022° F. (550° C.).

5. The process of claim 1 wherein the temperature of said first stream of gas comprising normally gaseous hydrocarbon compounds is in the range from about 932° F. (500° C.) to about 1292° F. (700° C.).

6. The process of claim 1 wherein said olefin hydrogenation zone is operated at conditions including a pressure from 10 psig to about 200 psig and a temperature from about 100° F. (38° C.) to about 400° F. (204° C.).

7. The process of claim 1 wherein said normally gaseous hydrocarbon compounds are selected from the group consisting of ethane, propane and butane.

* * * * *